United States Patent
Shekalim

(10) Patent No.: US 8,707,792 B2
(45) Date of Patent: Apr. 29, 2014

(54) DRUG DELIVERY DEVICE AND METHOD

(75) Inventor: Avraham Shekalim, Nesher (IL)

(73) Assignee: Nilimedix Ltd., Haifa (IL)

( * ) Notice: Subject to any disclaimer, the term of this patent is extended or adjusted under 35 U.S.C. 154(b) by 0 days.

(21) Appl. No.: 13/217,303

(22) Filed: Aug. 25, 2011

(65) Prior Publication Data
US 2012/0017688 A1  Jan. 26, 2012

Related U.S. Application Data

(62) Division of application No. 10/558,409, filed as application No. PCT/IL2004/000460 on May 30, 2004, now Pat. No. 8,021,334.

(51) Int. Cl.
*G01L 13/02* (2006.01)

(52) U.S. Cl.
USPC ............................................. 73/716; 73/736

(58) Field of Classification Search
USPC .................................................. 73/700–756
See application file for complete search history.

(56) References Cited

U.S. PATENT DOCUMENTS

| | | | |
|---|---|---|---|
| 3,720,201 A * | 3/1973 | Ramsey, III | 600/561 |
| 4,299,220 A | 11/1981 | Dorman | |
| 4,447,224 A | 5/1984 | DeCant, Jr. et al. | |
| 4,482,346 A | 11/1984 | Reinicke et al. | |
| 4,486,190 A | 12/1984 | Reinicke et al. | |
| 4,545,389 A * | 10/1985 | Schaberg et al. | 600/561 |
| 4,557,269 A * | 12/1985 | Reynolds et al. | 600/488 |
| 5,239,319 A | 8/1993 | Miyazaki et al. | |
| 5,405,614 A | 4/1995 | D'Angelo et al. | |
| 5,433,351 A | 7/1995 | Okayama et al. | |
| 6,117,086 A * | 9/2000 | Shulze | 600/488 |
| 6,248,093 B1 | 6/2001 | Moberg | |
| 6,497,680 B1 | 12/2002 | Holst et al. | |
| 6,635,020 B2 * | 10/2003 | Tripp et al. | 600/488 |
| 7,291,126 B2 | 11/2007 | Shekalim | |
| 7,377,907 B2 | 5/2008 | Shekalim | |
| 2007/0197922 A1 * | 8/2007 | Bradley et al. | 600/488 |
| 2009/0012464 A1 * | 1/2009 | Martin et al. | 604/82 |
| 2011/0046558 A1 * | 2/2011 | Gravesen et al. | 604/180 |
| 2011/0214504 A1 * | 9/2011 | Bradley et al. | 73/723 |

FOREIGN PATENT DOCUMENTS

| | | |
|---|---|---|
| DE | 3520782 | 5/1986 |
| EP | 1177802 | 2/2002 |
| WO | WO02070047 | 9/2002 |

* cited by examiner

*Primary Examiner* — Andre Allen
(74) *Attorney, Agent, or Firm* — Mark M. Friedman

(57) ABSTRACT

A drug delivery device (10) includes a pressurized reservoir (14) in communication with a flow path to an outlet (12). The flow path includes two normally-closed valves (16, 18) and a flow restriction (18). A pressure measurement arrangement (22) measures a differential fluid pressure between two points (24, 26) along the flow path which span at least part of the flow restriction (18), one of the points being between the valves (16, 18). A controller (28) selectively opens the valves (16, 18) to deliver a defined quantity of the liquid medicament to the outlet (12).

4 Claims, 18 Drawing Sheets

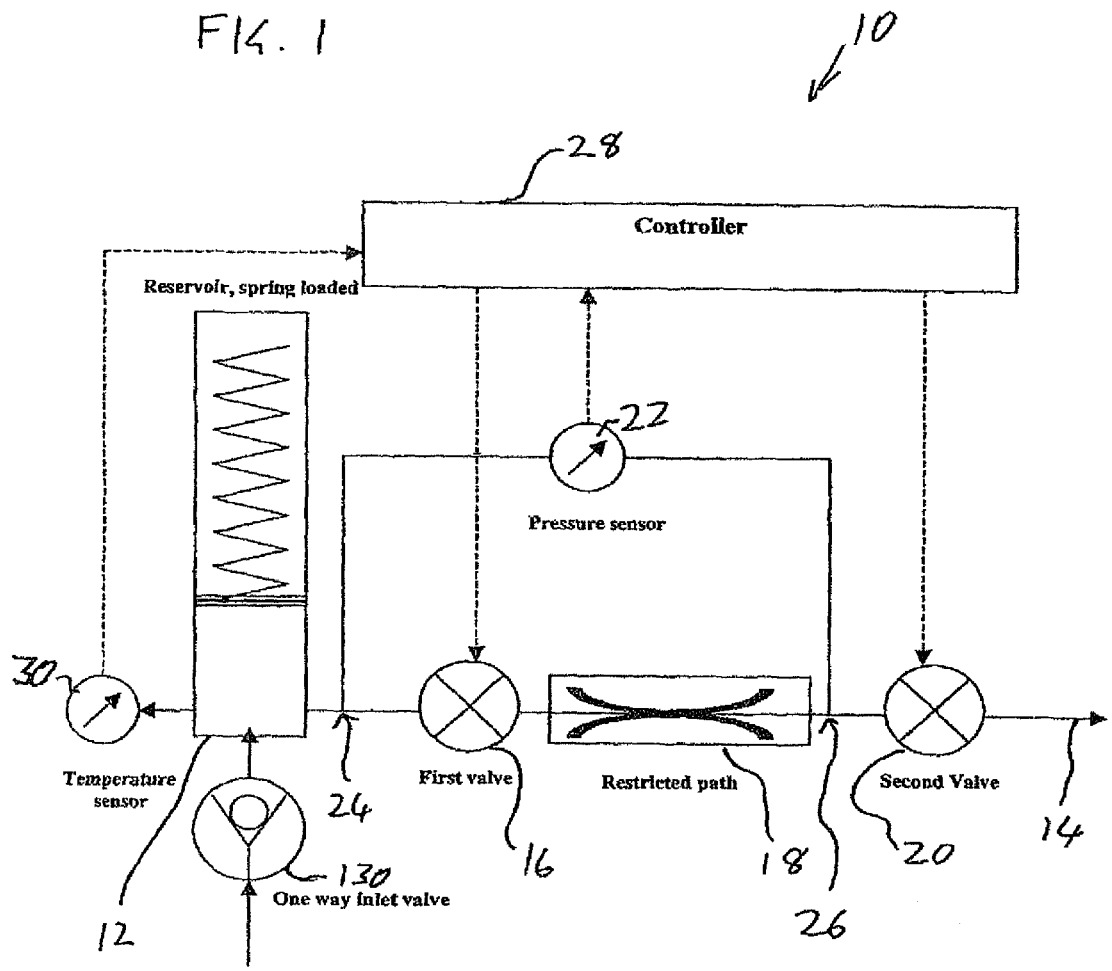

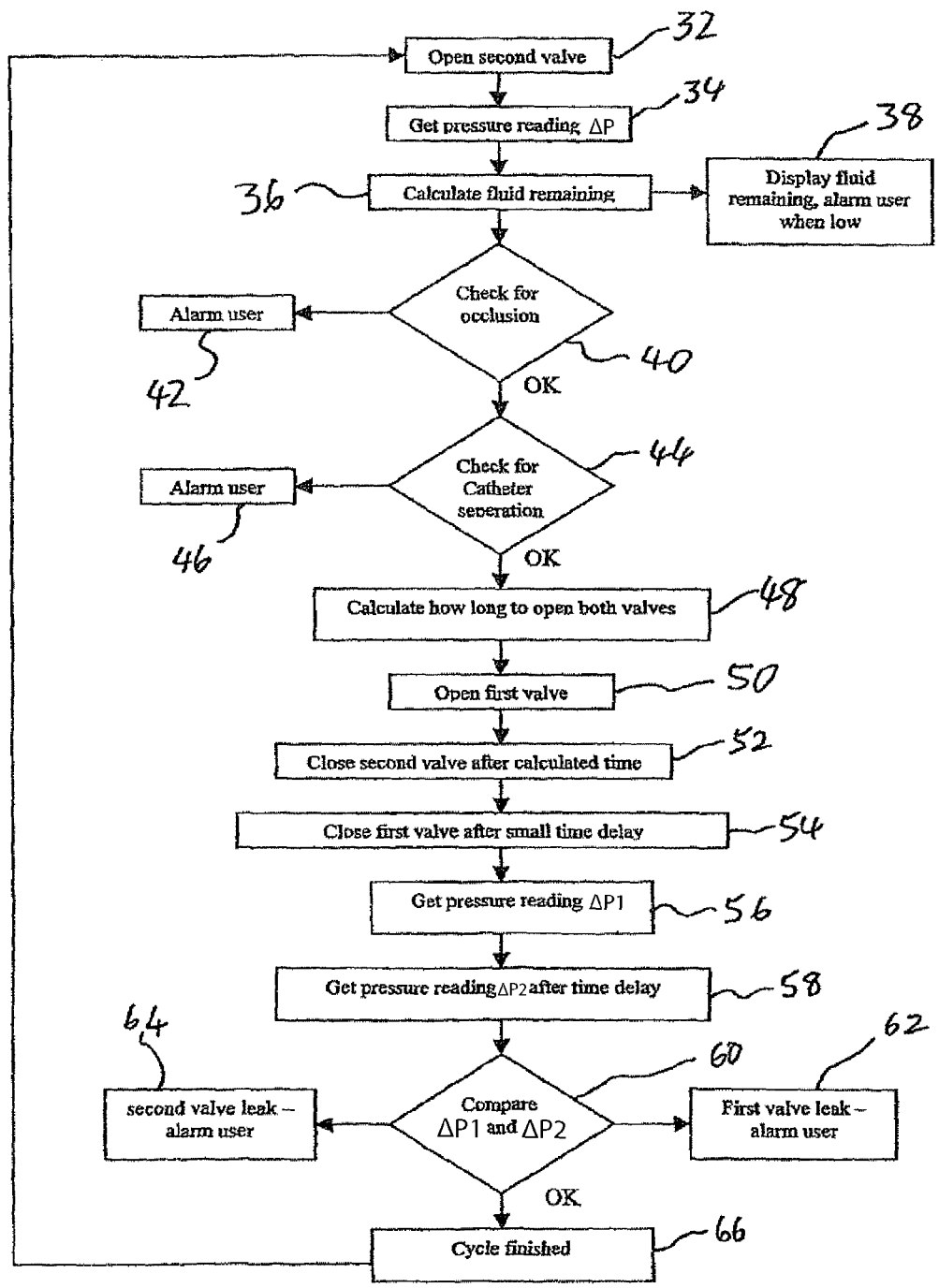

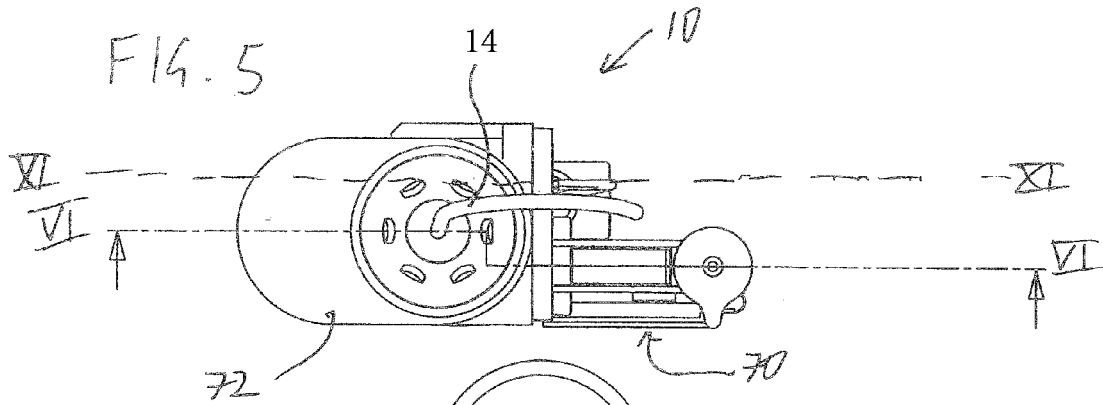
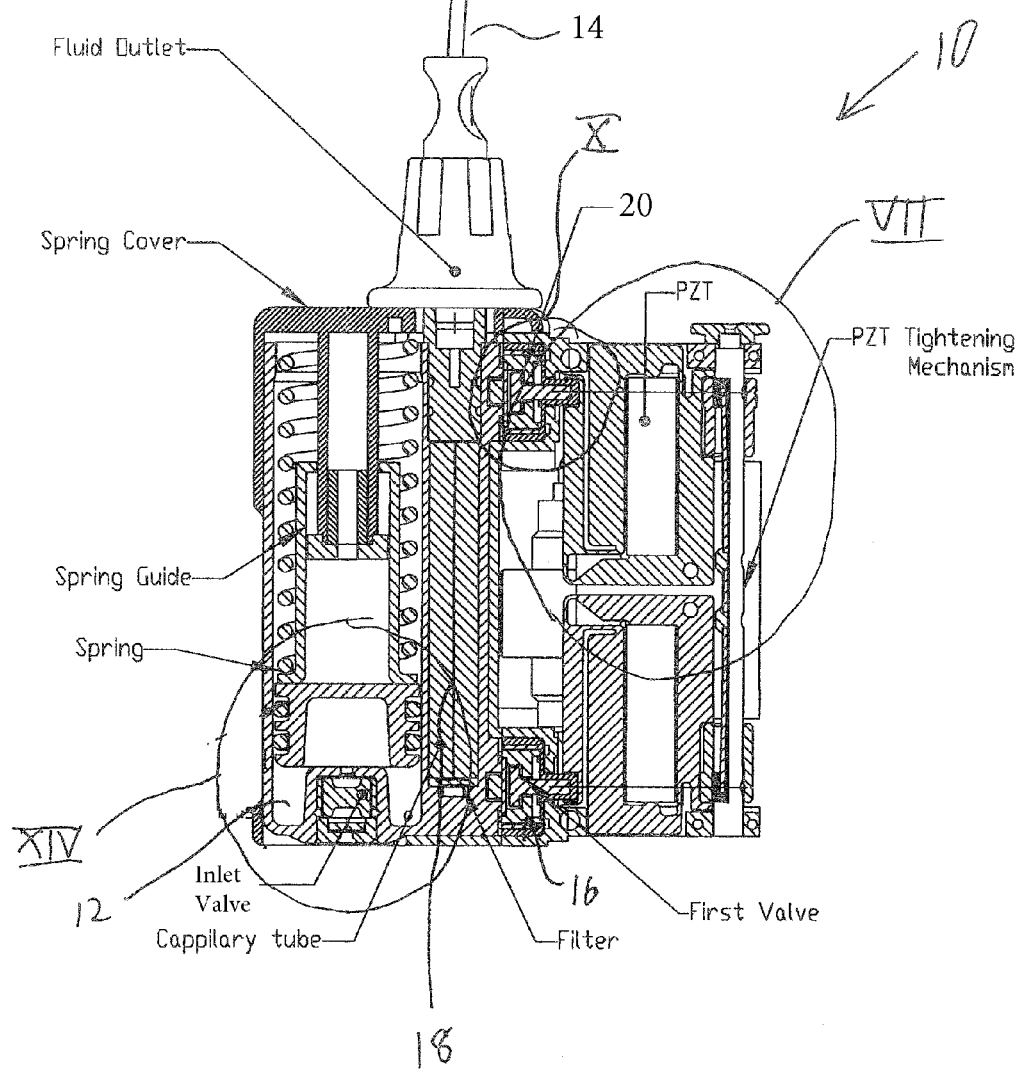

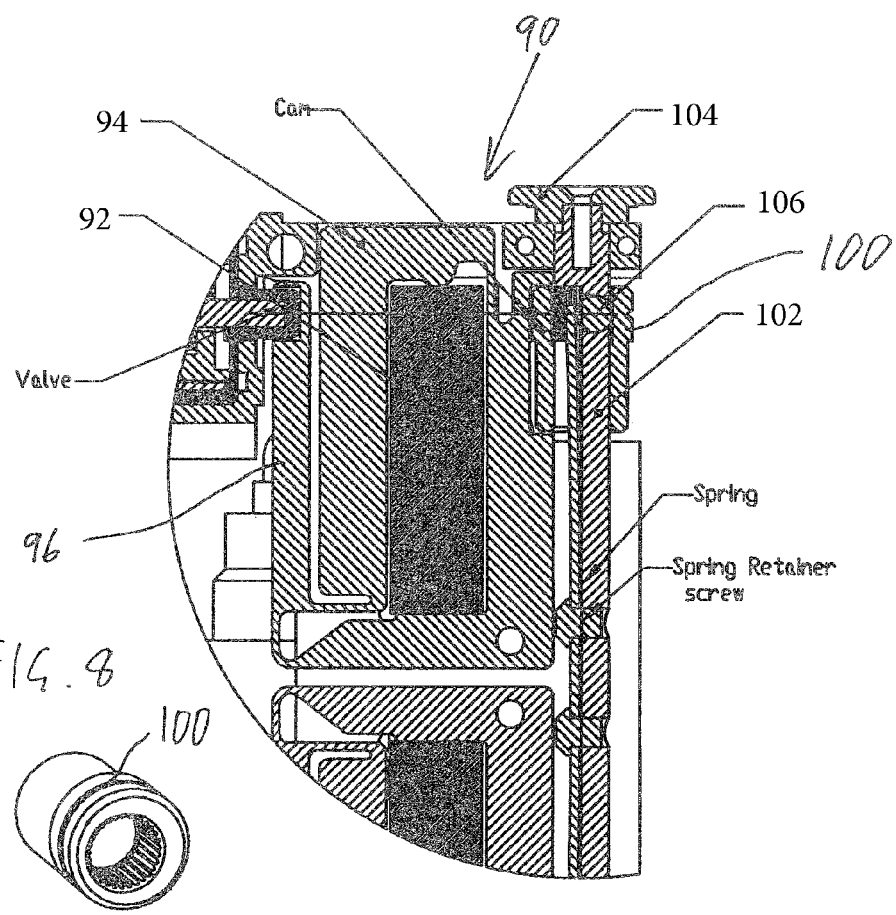
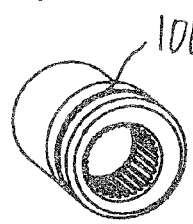
FIG. 7
FIG. 8

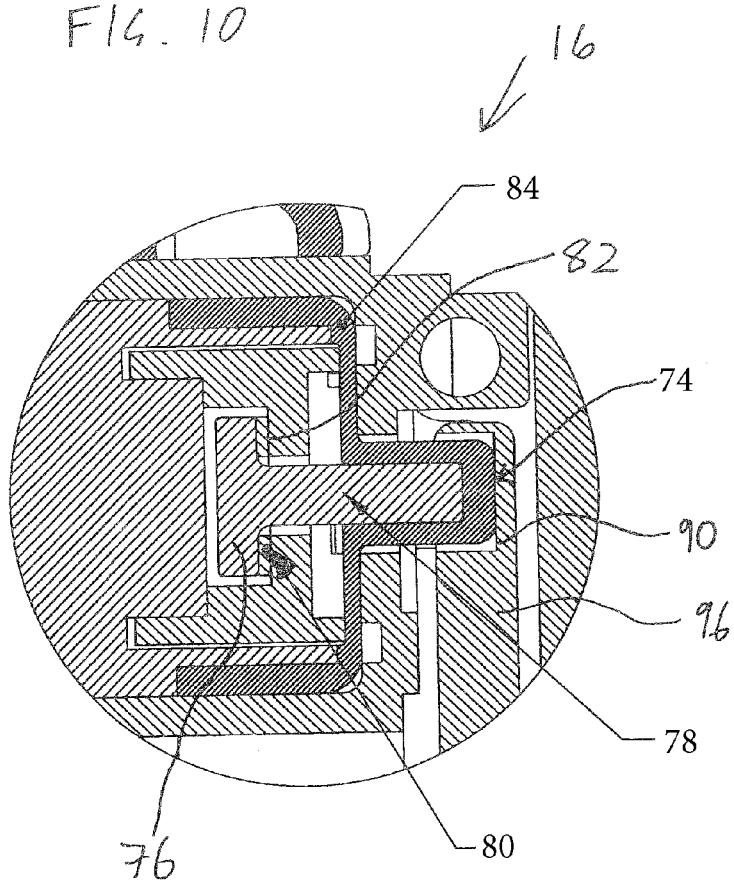

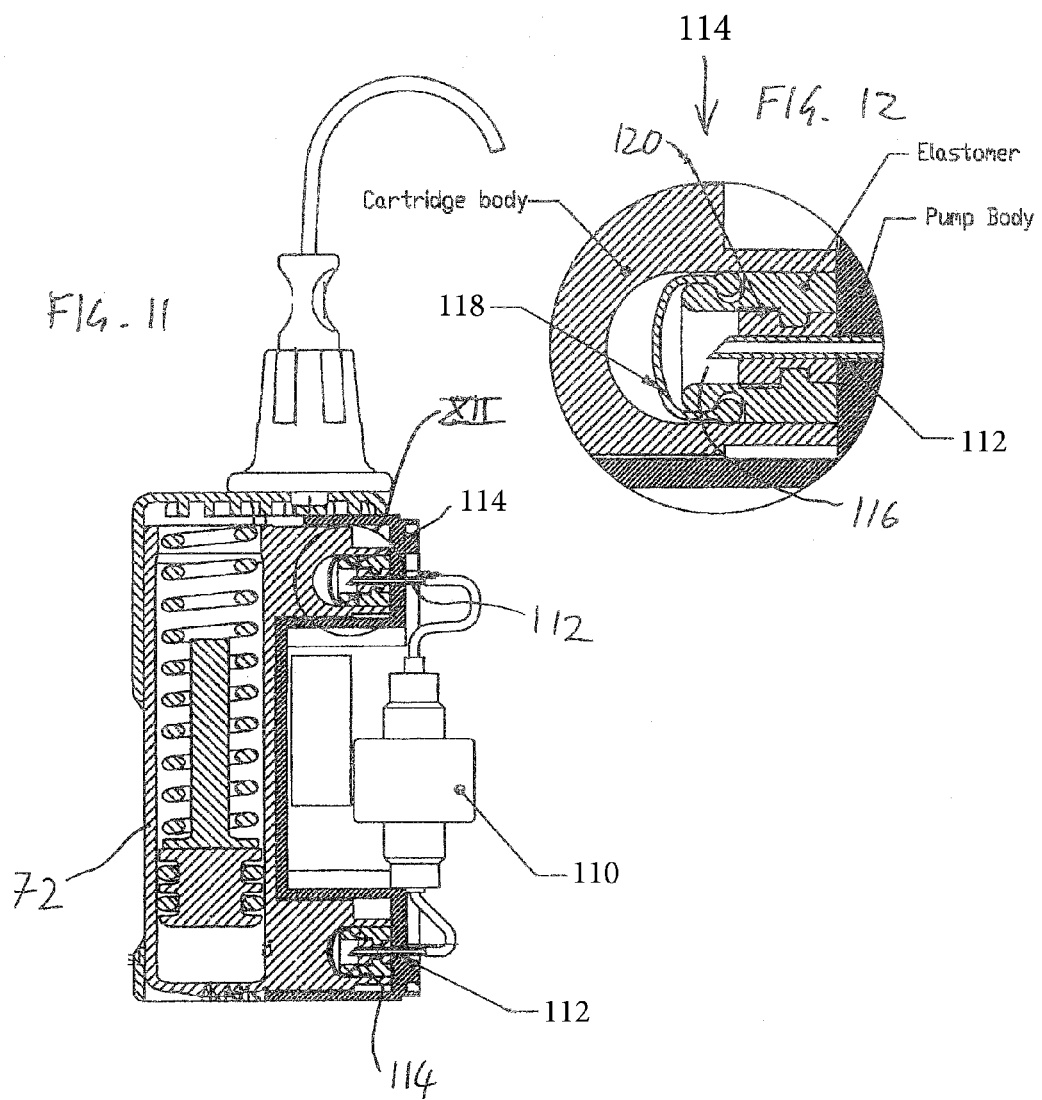

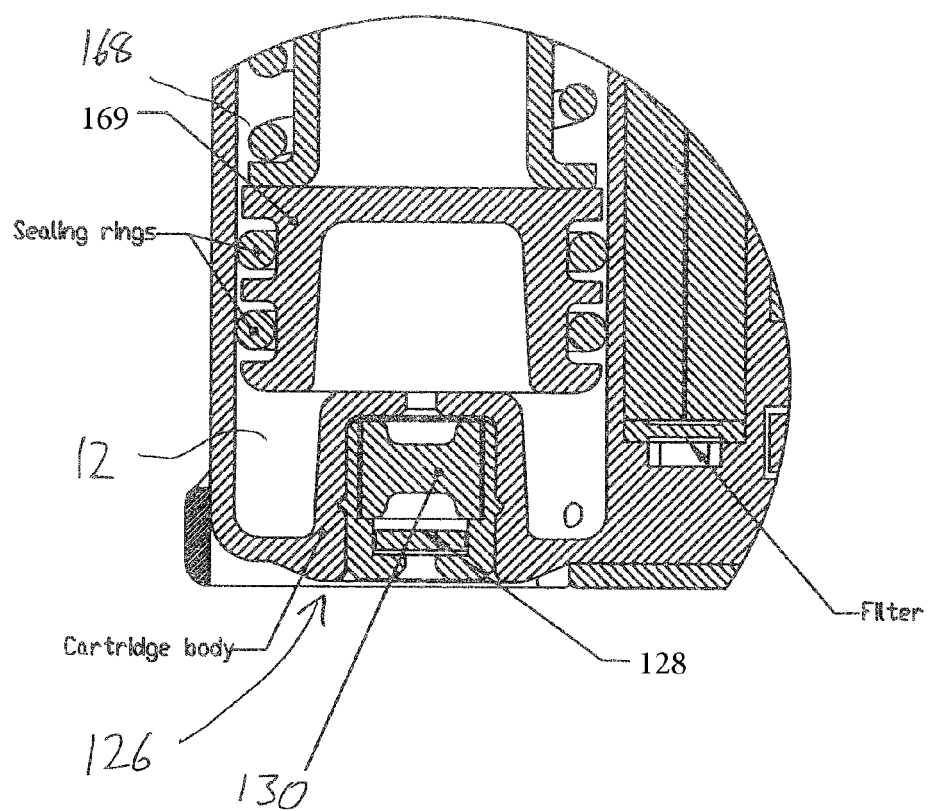

3. After capillary passage fluid goes to port and to second valve inlet

4. From second valve to cartridge exit

2. From first outlet to passage

1. High pressure from within cartridge goes to first valve inlet and to first port

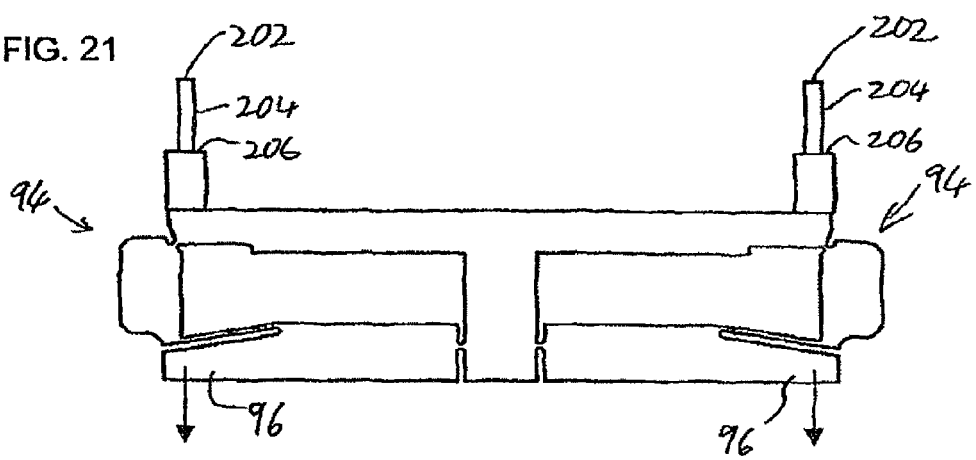
FIG. 21
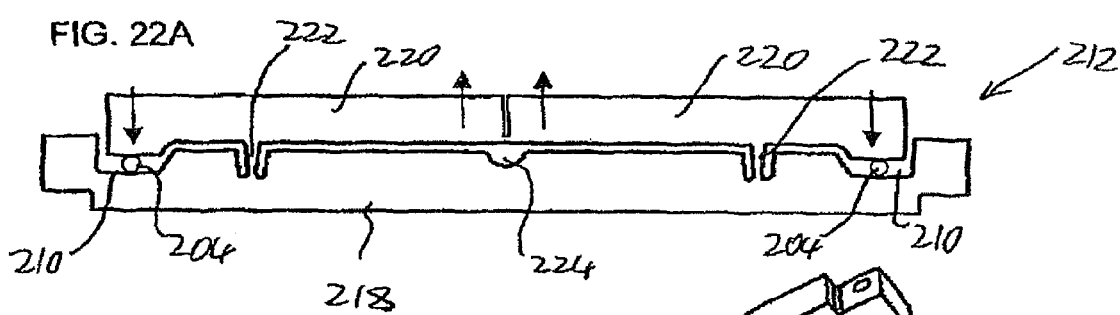
FIG. 22A
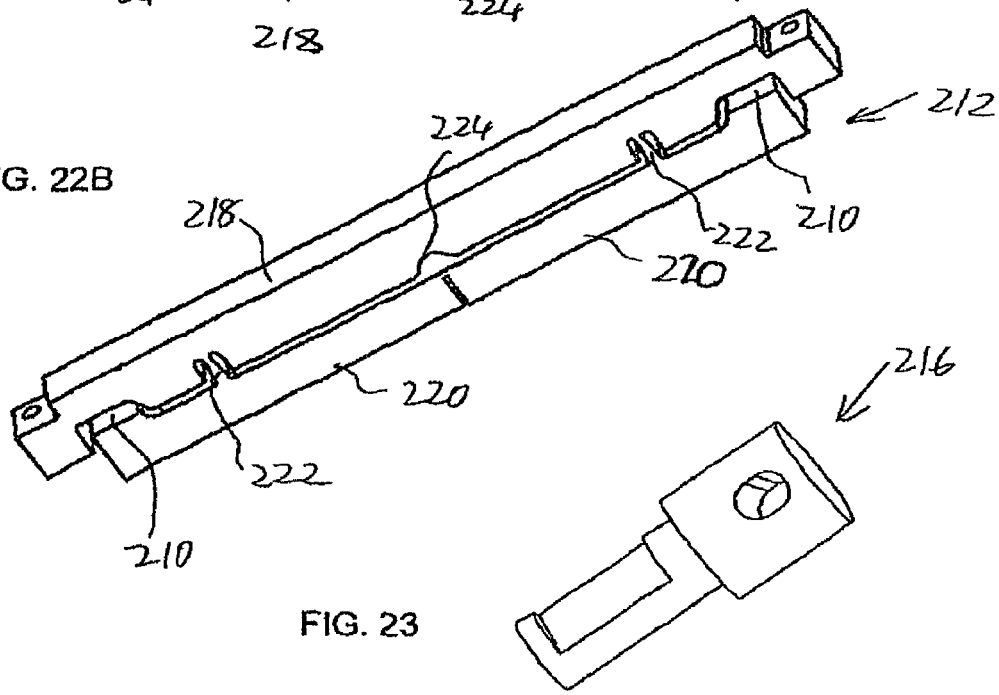
FIG. 22B
FIG. 23

DRUG DELIVERY DEVICE AND METHOD

FIELD AND BACKGROUND OF THE INVENTION

The present invention relates to drug delivery devices and, in particular, it concerns a drug delivery device and corresponding methods which employ a pressurized reservoir of liquid medicament with controlled release via a flow restriction and multiple valves.

Low-dosage infusion pumps, both external and implantable, have been developed to the point of commercial and medical acceptance. For certain applications, a simple "constant flow" device is sufficient. In many cases, however, where patients require adjustments in the dosage as a function of time, constant flow pumps are inadequate. A typical example is diabetes where the quantity of medication, such as insulin, to be infused varies due to requirements of the patient. Fluctuations can occur on a daily basis or more randomly as a function of the ingestion of food. Consequently, to address the shortcomings of constant flow devices and obtain significant flexibility in dosage rates, various "implantable programmable" pumps have been developed. In the definition of system requirements dealing with such implantable programmable pumps, a device which will provide programmable bolus and basal flow rates over a wide dynamic range is a standing system requirement. This requirement can be set forth in a practical sense by reference to the treatment of diabetes. It is known that the amount of medication, typically insulin, to be infused per unit of time, should be adjusted at certain time intervals. A patient's requirements may fluctuate either at set, known rates or may vary abnormally, for example, by the ingestion of food or by other transitory conditions. Those conditions will call for the administration of a bolus dose of infusate. In the daily administration of insulin, however, the patient may require a basal dose that is supplanted by bolus doses at, for example, meal times. The difference in flow rates between basal and bolus doses may be quite large, in the orders of several times. Thus, a device to achieve proper flow rates over the spectrum of desired rates must have the ability to continuously infuse, at very low flow rates, yet provide, periodically, a substantially increased flow rate. Thus, the design criteria can be summarized as requiring, in the first instance, the ability for continuous basal drug delivery which is adjustable to varying choices of flow rate, including the ability to deliver a bolus dose at relatively high flow rates.

The requirements of programmability, wide range of flow rates, and failsafe operation greatly complicate the design of programmable drug delivery devices. Secondary issues such as power consumption, overall system life and economic viability limit the feasibility of many of the theoretical solutions that have been proposed to-date.

In an attempt to ensure failsafe operation, many programmable drug delivery devices employ a negative-pressure storage chamber, effectively precluding the possibility of drug leakage in the case of device malfunction. Examples of such devices, referred to as "negative pressure pumps", may be found in U.S. Pat. Nos. 4,482,346 and 4,486,190. Both of these prior art devices are solenoid activated negative pressure pumps. A diaphragm storage chamber maintains the drug to be infused in a chamber having a diaphragm which separates the drug from propellant, normally freon, maintained at negative pressure. A solenoid is activated driving an armature and a bellows pumping element. This displacement of the armature opens a check valve which draws drug from the storage chamber into a downstream pumping chamber. A restriction will prevent backflow in the outlet during this short period. When the pump chamber is full, the check valve closes and the solenoid is then de-energized. A spring force typically displaces the bellows into the chamber pumping the drug through a restrictor and into the patient.

Negative pressure systems, while offering advantages of safety, suffer from major disadvantages. First, the negative pressure requirements require special precautions and equipment for filling and handling of the devices. Furthermore, since all of the drug must be positively displaced by a pump working against a pressure gradient, the devices have high power consumption, requiring bulky power sources and/or frequent battery replacement.

A second approach exemplified by U.S. Pat. Nos. 4,299,220 and 4,447,224 employs a positive pressure storage chamber in combination with an accumulator pump. The positive pressure of the storage chamber eliminates the handling problems of negative pressure devices. Where sufficiently high pressure is used to drive drug delivery without additional pumping, at least part of the power consumption is reduced, although many valve actuation elements are also consume a lot of power.

Despite the advantages of simplicity of implementation and energy efficiency, safety remains a major concern for positive pressure devices. Given the fact that drug chamber pressure is above body pressure, there remains a remote possibility for an overdose of drug should all valves in line with the output fail open at the same time. An improved degree of safety can be achieved in such systems by providing redundant valves. However, even with redundant valves, there remains some risk of multiple component failure which could result in overdosing. Depending upon the type of drug being administered, such overdosing could potentially be fatal.

A further problem associated with all types of programmable drug delivery devices is that of repeat usage. Throughout the field of medicine, there is a strong trend towards use of disposable components for infusion sets and the like. In the case of programmable drug delivery devices, the cost of the device is such that it is not presently feasible to produce single-use disposable devices. Furthermore, the subdivision of components between disposable "wet" components and reusable electronic and control components which is common in hospital infusion control systems such as the IVAC™ system is typically considered impractical here because of the extremely low flow rates and precision control required from such devices.

There is therefore a need for a programmable drug delivery device and corresponding methods of delivering drugs based upon a pressurized reservoir and which would reliably identify and appropriately address a range of malfunction conditions to avoid risk of drug overdosing. It would also be highly advantageous to provide a programmable drug delivery device and corresponding method facilitating subdivision of the device into reusable electronic and control components, and disposable components which come in contact with the drug. Finally, it would also be highly advantageous to provide a programmable drug delivery device which would have extremely low power consumption.

SUMMARY OF THE INVENTION

The present invention is a drug delivery device and corresponding method for metered delivery of a liquid medicament.

According to the teachings of the present invention there is provided, a drug delivery device for metered delivery of a liquid medicament to an outlet, the device comprising: (a) a pressurized reservoir configured for storing and supplying the liquid medicament at a pressure above atmospheric pressure; (b) a flow path in fluid communication with the pressurized reservoir and the outlet, the flow path including: (i) a first valve assuming a normally-closed flow-blocking state and selectively actuatable to an open state which permits fluid flow through the first valve, (ii) a flow restriction configured to limit fluid flow along the flow path, and (iii) a second valve assuming a normally-closed flow-blocking state and selectively actuatable to an open state which permits fluid flow through the second valve, such that, when both the first valve and second valve are in the open state, the liquid medicament flows from the pressurized reservoir along the flow path to the outlet at a rate limited primarily by the flow restriction; (c) a pressure measurement arrangement deployed in pressure-sensing engagement with a first point and a second point along the flow path, at least part of the flow restriction being between the first and second points, one of the first and second points being intermediate to the first and second valves; and (d) a controller electronically associated with the pressure measurement arrangement and the first and second valves, and configured to selectively open the first and second valves to deliver a defined quantity of the liquid medicament to the outlet.

According to a further feature of the present invention, the pressure measurement arrangement is configured to determine a differential pressure between fluid at the first and second points.

According to a further feature of the present invention, the controller is configured to: (a) actuate the first and second valves such that the first and second valves close sequentially, thereby trapping a quantity of the liquid medicament between the first and second valves with a pressure differential across the first valve; (b) while the first and second valves are closed, monitor measurements of the pressure measurement arrangement; and (c) if the measurements vary so as to indicate a reduction in the pressure differential across the first valve, generate a malfunction indication.

According to a further feature of the present invention, the controller is configured to: (a) actuate the first and second valves such that the first and second valves close sequentially, thereby trapping a quantity of the liquid medicament between the first and second valves with a pressure differential across the second valve; (b) while the first and second valves are closed, monitor measurements of the pressure measurement arrangement; and (c) if the measurements vary so as to indicate a reduction in the pressure differential across the second valve, generate a malfunction indication.

According to a further feature of the present invention, the pressurized reservoir includes an elastic pressurizing member such that a fluid pressure within the reservoir varies as a function of a volume of the liquid medicament currently stored, and wherein the controller is configured to: (a) estimate a remaining volume of the liquid medicament in the reservoir based upon at least one measurement from the pressure measurement arrangement obtained under zero flow conditions; and (b) if the remaining volume is less than a minimum volume value, generate a low-remaining-volume indication.

According to a further feature of the present invention, the controller is configured to: (a) during operation of the drug delivery device, repeatedly: (i) selectively actuate one of the first and second valves to the open state such that the pressure measurement arrangement measures a value of a differential fluid pressure under zero flow conditions between the reservoir and the outlet, and (ii) store the differential fluid pressure values; (b) monitor the stored values to identify an increase in the values relative to a mean peak pressure difference; and (c) if an increase in the values is identified, generate a disconnection indication.

There is also provided according to the teachings of the present invention, in a drug delivery device having a pressurized source of a liquid medicament supplying a flow path including two valves and a flow restriction, a method for identifying malfunction of at least one of the valves, the method comprising: (a) closing both valves in such a manner as to ensure a pressure differential across at least one of the valves; and (b) monitoring for a change in liquid pressure between the valves.

There is also provided according to the teachings of the present invention, a fluid drug delivery device comprising: (a) a cartridge including a fluid supply assembly, a fluid outlet, and a flow control arrangement including a flow control valve, the flow control arrangement controlling flow from the fluid supply assembly to the fluid outlet, the flow control valve being operated by displacement of at least one actuation surface provided by the cartridge, the actuation surface being isolated from contact with the fluid; (b) a portable base unit configured for receiving the cartridge in removable engagement with the base unit, the base unit including: (i) a processing unit, (ii) a piezoelectric actuator controlled by the processing unit, and (iii) a mechanical amplifier associated with the piezoelectric actuator and configured to produce an output displacement at an output surface, the output displacement having an amplitude greater than an output displacement of the piezoelectric actuator; and (c) an adjustment mechanism associated with one of the cartridge and the base unit, the adjustment mechanism being operative, after engagement of the cartridge with the base, to bring the output surface of the mechanical amplifier into contact with the actuation surface.

There is also provided according to the teachings of the present invention, a pressure measurement interface for measuring fluid pressure within a disposable arrangement defining a fluid flow path by use of a reusable pressure sensor, the interface including: (a) a disposable pressure sensing cell deployed in fluid connection with the fluid flow path, the pressure sensing cell including a closed liquid-filled sensing volume isolated from fluid in the fluid flow path by a flexible membrane, the sensing volume having a first portion of a mating configuration; and (b) a second portion of a mating configuration associated with the reusable pressure sensor and configured for mating with, the first portion of the mating configuration so as to form fluid interconnection between the pressure sensor and the liquid-filled sensing volume.

There is also provided according to the teachings of the present invention, a fluid drug delivery device comprising: (a) a pressurized fluid reservoir configured for storing and supplying the fluid drug at a pressure above atmospheric pressure; (b) a flow regulating system associated with the fluid reservoir and configured to control flow from the fluid reservoir to a fluid outlet, the flow regulating system including a controller operative to detect at least one predefined malfunction condition; and (c) a reservoir pressure release mechanism associated with the controller so as to be actuated in response to the malfunction condition to depressurize the reservoir, thereby interrupting flow from the fluid reservoir to the outlet.

BRIEF DESCRIPTION OF THE DRAWINGS

The invention is herein described, by way of example only, with reference to the accompanying drawings, wherein:

FIG. 1 is a schematic representation of a drug delivery device, constructed and operative according to the teachings of the present invention;

FIG. 2 is a flow chart illustrating the sequence of operation of the drug delivery device of FIG. 1;

FIG. 5 is a top view of the device of FIG. 4;

FIG. 6 is a split-level cross-sectional view taken along the line VI-VI in FIG. 5;

FIG. 7 is an enlarged view of the portion of FIG. 6 designated VII;

FIG. 8 is an isometric view of a cam tightening element from FIG. 7;

FIG. 10 is an enlarged view of the portion of FIG. 6 designated X;

FIG. 11 is a cross-sectional view taken along the line XI-XI in FIG. 5;

FIG. 12 is an enlarged view of the region of FIG. 11 designated XII;

FIG. 13 is an enlarged view of the region of FIG. 6 designated XIV;

FIGS. 14A-14F are schematic views of the removable cartridge of FIG. 4 together illustrating the flow path of a liquid medicament defined by the cartridge, wherein:

FIG. 14A is a side view of the removable cartridge showing its docking ports;

FIG. 14B is a cross-sectional view taken along line S-S of FIG. 14A;

FIGS. 14C-14F are cross-sectional views taken through FIGS. 14A and 14B along the lines R-R, V-V, Q-Q and T-T, respectively;

FIG. 21 is a front view of a mechanical amplifier from the piezoelectric actuator implementation of FIG. 19;

FIGS. 22A and 22B are a side view and an isometric view, respectively, of a locking lever arrangement from the piezoelectric actuator implementation of FIG. 19; and FIG. 23 is an isometric view of an eccentric locking rod from the piezoelectric actuator implementation of FIG. 19.

DESCRIPTION OF THE PREFERRED EMBODIMENTS

Figures 3A, 3B, 3C:
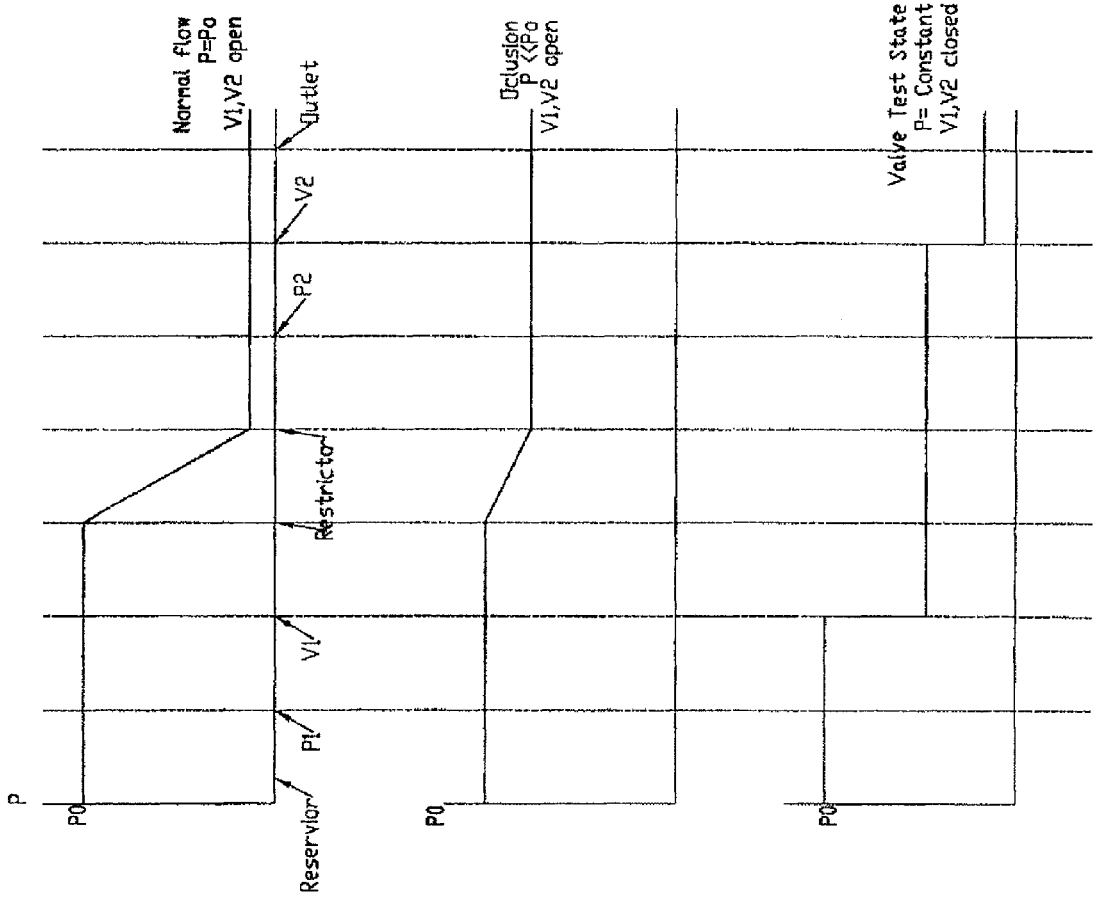
FIG. 3A is a graph of the drug delivery device of FIG. 1 dining normal flow with a first and second valves in an open state.
FIG. 3B is a graph similar to FIG. 3A illustrating the variation in fluid pressure along the flow path in the presence of a partial occlusion of outlet flow.
FIG. 3C is a graph illustrating the variation in fluid pressure along the flow path during a valve-testing sequence with the first and second valves closed.

The present invention is a drug delivery device and corresponding method for metered delivery of a liquid medicament.

The principles and operation of devices and methods according to the present invention may be better understood with reference to the drawings and the accompanying description.

Before addressing the details of the present invention, it should be noted that numerous features of the invention are believed to be of patentable significance alone, independent of the other features described herein. Examples of features believed to be patentable include but are not limited to: the apparatus and methods for detecting valve malfunction; the apparatus and methods for detecting full and/or partial occlusion; the apparatus and methods for detecting drug reservoir content; the apparatus and methods for detecting disconnection of a drug delivery set; the low power consumption valve actuator arrangement; the apparatus and method for emergency reservoir pressure release; and the apparatus and method for employing reusable pressure sensors to measure fluid pressure within a disposable cartridge without compromising sterility of the cartridge contents. For the purpose of conciseness, the various features will be described herein in one or more preferred implementations which combine most, or all, of these features. It will be clear, however, to one ordinarily skilled in the art, that the various features may equally be implemented in a range of other contexts and may be used independently in otherwise conventional systems.

Referring now to the drawings, FIGS. 1-14F illustrate the structure and operation of a drug delivery device, generally designated 10, constructed and operative according to the teachings of the present invention, for metered delivery of a liquid medicament to an outlet 12, typically connected to an infusion set (not shown).

Referring specifically to the schematic representation of FIG. 1, generally speaking, device 10 has a pressurized reservoir 14 configured for storing and supplying the liquid medicament at a pressure above atmospheric pressure, and a flow path in fluid communication with pressurized reservoir 14 and outlet 12. The flow path includes a first valve 16, a flow restriction 18 configured to limit fluid flow along the flow path, and a second valve 20. Each of valves 16 and 20 assumes a normally-closed flow-blocking state and is selectively actuatable to an open state which permits fluid flow therethrough. When both the valves 16 and 20 are in the open state, the liquid medicament flows from the pressurized reservoir along the flow path to the outlet at a rate limited primarily by the flow restriction (corresponding to the fluid pressure distribution illustrated in FIG. 3A).

Device 10 also has a pressure measurement arrangement 22 deployed to measure a differential fluid pressure between a first point 24 and a second point 26 along the flow path. At least part of flow restriction 18 is located within the flow path between pressure measurement points 24 and 26, and one of the pressure measurement points 24 or 26 is positioned in the flow path between valves 16 and 20. In the preferred examples illustrated here, the first pressure measurement point 24 is located to measure the reservoir pressure prior to first valve 16 while the second measurement point 26 is between the valves distal to the flow restriction. It should be noted, however, that substantially equivalent functionality for all features described below can be achieved by positioning the first measurement point between the valves proximal to the flow restriction and the second measurement point distal to the second valve, all consequent required changes being self-explanatory to one ordinarily skilled in the art.

A controller 28 is electronically associated with pressure measurement arrangement 22 and first and second valves 16 and 20, and is configured to selectively open the valves to deliver a defined quantity of the liquid medicament to the outlet. Preferably, controller 28 is configured to actuate pulsed opening of first and second valves 16, 20 between the normally-closed state and the open state so that the fluid flow pulses provide a desired rate of delivery. The total valves-open time for each pulse is preferably calculated on the basis of an anticipated rate of flow determined from a measured fluid differential pressure during zero flow conditions between flow pulses. This calculation is based upon predetermined information about the fluid medicament viscosity, optionally supplemented by fluid temperature data obtained by a temperature sensor 30. Alternatively, or additionally, the actual rate of flow can be monitored by measuring the pressure differential across restriction 18 during the pulse. This information can either be used to modify the valves-open time of the present pulse, or in calculating the duration of the subsequent pulse.

It will be immediately apparent that the present invention provides a particularly simple and energy efficient programmable drug delivery system in which a relatively high reservoir storage pressure provides all the energy required to deliver the drug to the subject. At the same time, the combination of two independently switchable valves 16, 20 and pressure measurement arrangement 22 provides highly effective and near-immediate detection of a wide range of malfunction conditions, thereby ensuring extremely high levels of safety, as will now be detailed with reference to FIG. 2.

Figures 3D, 3E, 3F:
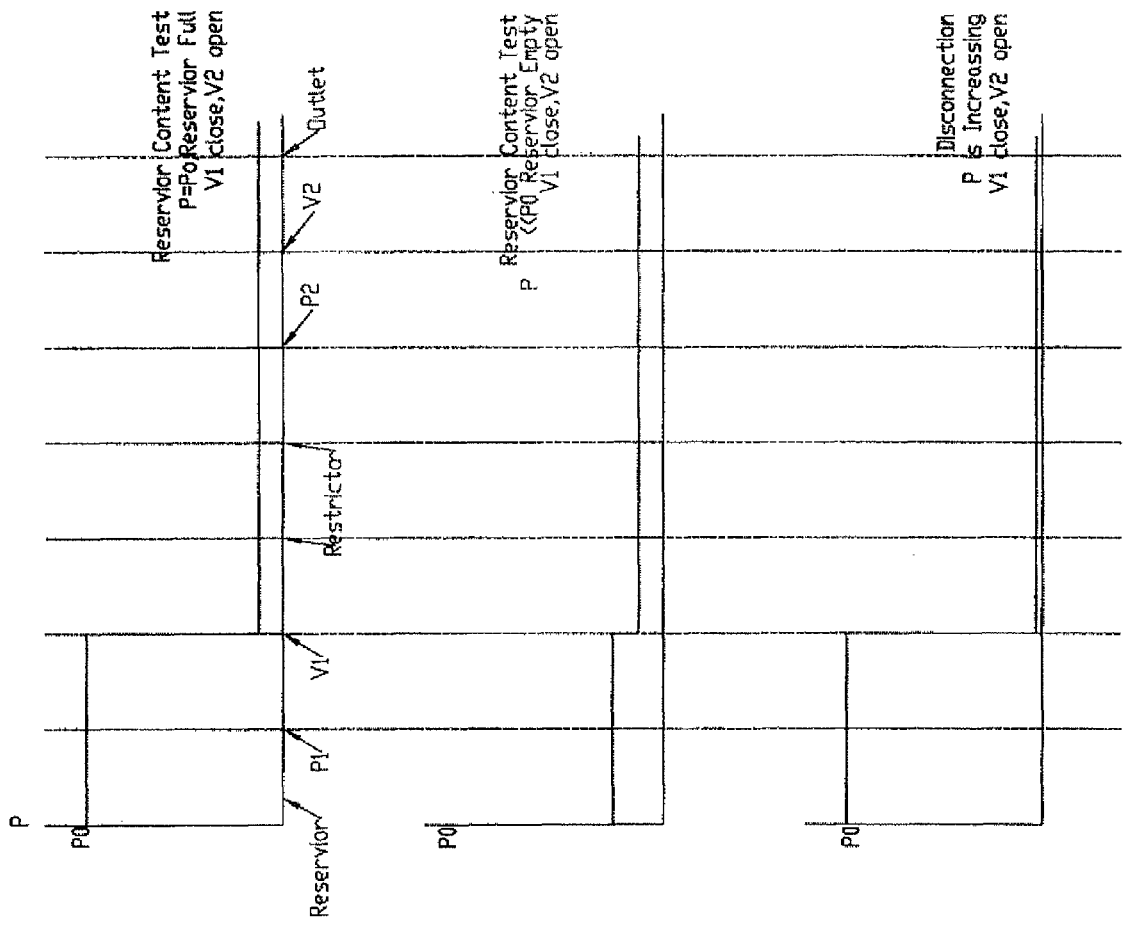
FIG. 3D is a graph illustrating the variation in fluid pressure along the flow path during a pressure test sequence under normal operating conditions with the first valve closed and the second valve open.
FIG. 3E is a graph similar to FIG. 3D when the drug reservoir is near empty.
FIG. 3F is a graph similar to FIG. 3D when the infusion set is disconnected.

Turning now to FIG. 2, this illustrates a preferred sequence of operation of device 10. First, at step 32, controller 28 opens second valve 20 while leaving valve 16 closed, and pressure difference $\Delta P$ is measured (step 34). In this zero-flow state, the pressure distribution along the flow path under normal conditions looks as illustrated in FIG. 3D. Here, the first pressure measurement point 24 of pressure measurement system 22 is exposed to the current pressure of the reservoir, while the second pressure measurement point 26 is at outlet pressure which typically corresponds to the subcutaneous body-fluid pressure. As a result, $\Delta P$ is effectively a measurement of the reservoir pressure less a relatively small, relatively constant value.

This state is particularly useful for a number of device self-tests, as follows. Firstly, it is a particularly preferred feature of the invention that pressurized reservoir 12 includes an elastic pressurizing member, typically a spring-driven piston, such that a fluid pressure within the reservoir varies as a function of a volume of the liquid medicament currently stored. As a result, the measured pressure differential $\Delta P$ is indicative of the remaining volume of the liquid medicament in reservoir 12. Thus, at step 36, controller calculates from the measured pressure differential a volume of fluid remaining in the reservoir and, at step 38, if the remaining volume is less than a minimum allowed volume value, controller 28 generates a low-remaining-volume indication. FIG. 3E illustrates the fluid pressure distribution which occurs in this test state when the reservoir is near empty.

In addition to warning of low remaining volume, the remaining fluid quantity calculation is also preferably used to compare with the expected values based upon the quantity of fluid which has been delivered by the device. If a discrepancy between the expected quantity of fluid remaining and the quantity indicated by the measured pressure differential is determined to be significant according to some predefined criteria, a malfunction indication is generated.

In most preferred cases, maximum reservoir operating pressure is in the range of 4-10 atmospheres. Operating pressures in excess of about 4 atmospheres (i.e., about 3 atmospheres above ambient atmospheric pressure) are particularly preferred due to the enhanced ability to dislodge blockages throughout the flow path due to the build-up of pressure behind the blockage. Since the outlet pressure is typically only very slightly above atmospheric pressure, the value of $\Delta P$ can typically be used as if it were a direct measurement of the reservoir pressure relative to atmospheric pressure.

Next, at step 40, controller 28 checks for occlusion downstream of the device as evidenced by residual elevated pressure beyond the closed valve 16. This would lead to a reduced reading of $\Delta P$. This case can be distinguished from the case of depletion of the reservoir contents by a large discrepancy between the expected remaining drug volume (original volume less the amount delivered) and the remaining drug volume as calculated from the $\Delta P$ value. If at step 40 an unexpected drop in $\Delta P$ is detected, an alarm signal is generated (step 42).

Then, at step 44, controller 28 checks whether the infusion set or other output connection has become disconnected. This case can be identified by an increase in the measured value of $\Delta P$ as illustrated in FIG. 3F. Since the variations in outlet pressure between the connected and disconnected states are small relative to the pressure difference between the reservoir and the output, reliable detection of disconnection requires comparison of the $\Delta P$ value with one or more previously measured valve. Most preferably, one or more most-recently sampled values of $\Delta P$ is compared with the statistical distribution of values of $\Delta P$ from previous cycles to determine whether there has been a statistically significant increase in pressure difference. If such an increase is detected, an alarm indication is generated at step 46.

Then, at step 48, the required valves-open flow pulse time is calculated and, at step 50, first valve 16 is opened to allow commencement of a flow pulse. Optionally, if the pulse duration is sufficient to allow the pressure distribution to reach substantially steady state, monitoring of pressure difference $\Delta P$ during the pulse can be used to provide additional measurement of the actual flow rate and/or to provide early warning of partial occlusion. Specifically, FIG. 3A shows a pressure distribution during normal steady-state flow conditions whereas FIG. 3B shows a similar distribution where a partial obstruction is present downstream. In the latter case, the measured value of $\Delta P$ drops significantly during the fluid flow pulse but returns to its full value when measured under zero flow conditions at step 34. These measurements are used to calculate a corrected pulse length to ensure that the required dosage is delivered despite the reduced flow rate through the device. Additionally, the device may provide an early warning to the user or to a medical practitioner of possible impending occlusion so as to allow preventative correction before full occlusion occurs.

Parenthetically, it should be noted that, in many low dosage rate applications, the compliance of the device (i.e. capacity of the system components to expand to accommodate additional fluid volume) is sufficient to accommodate the entire volume of a single fluid flow pulse downstream of the flow restriction 18 even if the outlet is partially occluded. In this case, so long as the pulse volume passes the obstruction and the pressure downstream of the valves returns to normal outlet pressure in the period between successive pulses, the total volume of drug delivered in each pulse is substantially unaffected by the partial occlusion.

A further particularly preferred feature of the present invention is the performance of a valve function test, most preferably during each flow pulse cycle of the system. Conceptually, the valve function test is performed by closing both valves so as to trap a pressure differential across at least one of the valves and monitoring the pressure for a defined period to test whether leakage has occurred across the valve. Most preferably, by trapping a pressure intermediate between the reservoir pressure and the outlet pressure, it is possible to ensure a pressure differential across both valves simultaneously, thereby allowing testing of both valves for leakage simultaneously.

Referring again to FIG. 2, the valve test is performed as follows. At the end of the designated flow pulse time, second valve 20 is closed first (step 52) followed by closing of first valve 16 after a small time delay (step 54). This fixes the pressure distribution as illustrated in FIG. 3C with a pressure differential across both valves 16 and 20. At step 56, a first reading of the differential pressure $\Delta P_1$ between points 24 and 26 is taken. After a given time delay, a second differential pressure reading $\Delta P_2$ is taken (step 58) and the values are compared (step 60). If the differential pressure has dropped ($\Delta P_2 < \Delta P_1$), this indicates that the pressure between the valves has increased due to leakage across first valve 16 and a corresponding alarm indication is generated (step 62). If the differential pressure increases ($\Delta P_2 > \Delta P_1$), this indicates that the pressure between the valves has dropped due to leakage across second valve 20 and a corresponding alarm indication is generated (step 64). If no malfunction is detected ($\Delta P_1 = \Delta P_2$), the flow pulse cycle terminates at 66 and the entire cycle repeats from step 32.

Turning now to FIGS. 4-14F, these illustrate a preferred implementation of device 10. In addition to incorporating all of the structural features and functionality described above with reference to FIGS. 1-3F, this implementation also illustrates important features relating to subdivision of components between a reusable body and a disposable cartridge, and further illustrates power-saving actuator configurations, as will now be described.

Referring specifically to the overall views of FIGS. 4-6 and 11, these show device 10 made up of a body 70 and a removable cartridge 72. Pressurized reservoir 12 and the entire flow path including valves 16 and 20 and flow restriction 18 are implemented as part of removable cartridge 72, while the controller and it's associated electronic components are implemented as part of body 70. This subdivision, which offers profound advantages with regard to the economic viability of the device, is non-trivial to implement due to the difficulty of achieving precise valve actuation and pressure measurement while all electronic components remain part of the reusable body 70. Preferred solutions to these difficulties according to the teachings of the present invention will now be described.

Referring now to the valve structures shown, first and second valves 16 and 20 are here implemented as part of replaceable cartridge 72. As seen in the enlarged view of FIG. 10, each valve has an externally exposed actuator surface 74, isolated from the fluid flow path through the valve, so that force applied to actuator surface 74 actuates the valve to assume its open state. In the implementation shown here, the valve has a head 76 integrally formed with a valve stem 78. Valve head 76 has an elastomeric sealing ring 80 which seals against valve seat 82. In the implementation shown here, valve stem 78 is supported and biased to its closed position by an elastomeric diaphragm 84 which also provides an external seal for the flow path through the valve. The external surface of diaphragm 84 at the rear of valve stem 78 provides the aforementioned actuator surface 74 such that force applied to surface 74 displaces the valve head away from its seat so as to open the valve without exposing the fluid flow path to any external contamination. Actuator surface 74 is shown here engaged by an output surface of an actuator assembly 90 which is included in body 70, to be described with reference to FIGS. 7-9 and 19-23.

Returning to FIG. 6, there can be seen a pair of actuator assemblies 90 which are each deployed for engaging the actuator surface 74 of one of valves 16, 20. A first preferred implementation for actuator assemblies 90 is shown enlarged in FIG. 7. An alternative preferred implementation will be described below with reference to FIGS. 19-23. By way of introduction, piezoelectric actuators are known to have low power consumption and would therefore be ideal for battery-powered drug delivery devices such as that of the present invention. Nevertheless, they are not commonly used due to the very limited displacements which they typically provide. Furthermore, though it may be feasible to build a small-displacement high-precision valve to be actuated by a piezoelectric actuator, this becomes impractical where the valve is part of a low-cost disposable cartridge, and where the actuator and valve are located in separable components with insufficient precision of interrelation between them when they are brought together. To address these issues, the present invention combines a piezoelectric actuator with both a mechanical amplifier and an alignment adjustment mechanism to render use of power-efficient piezoelectric actuators feasible.

Figure 9:
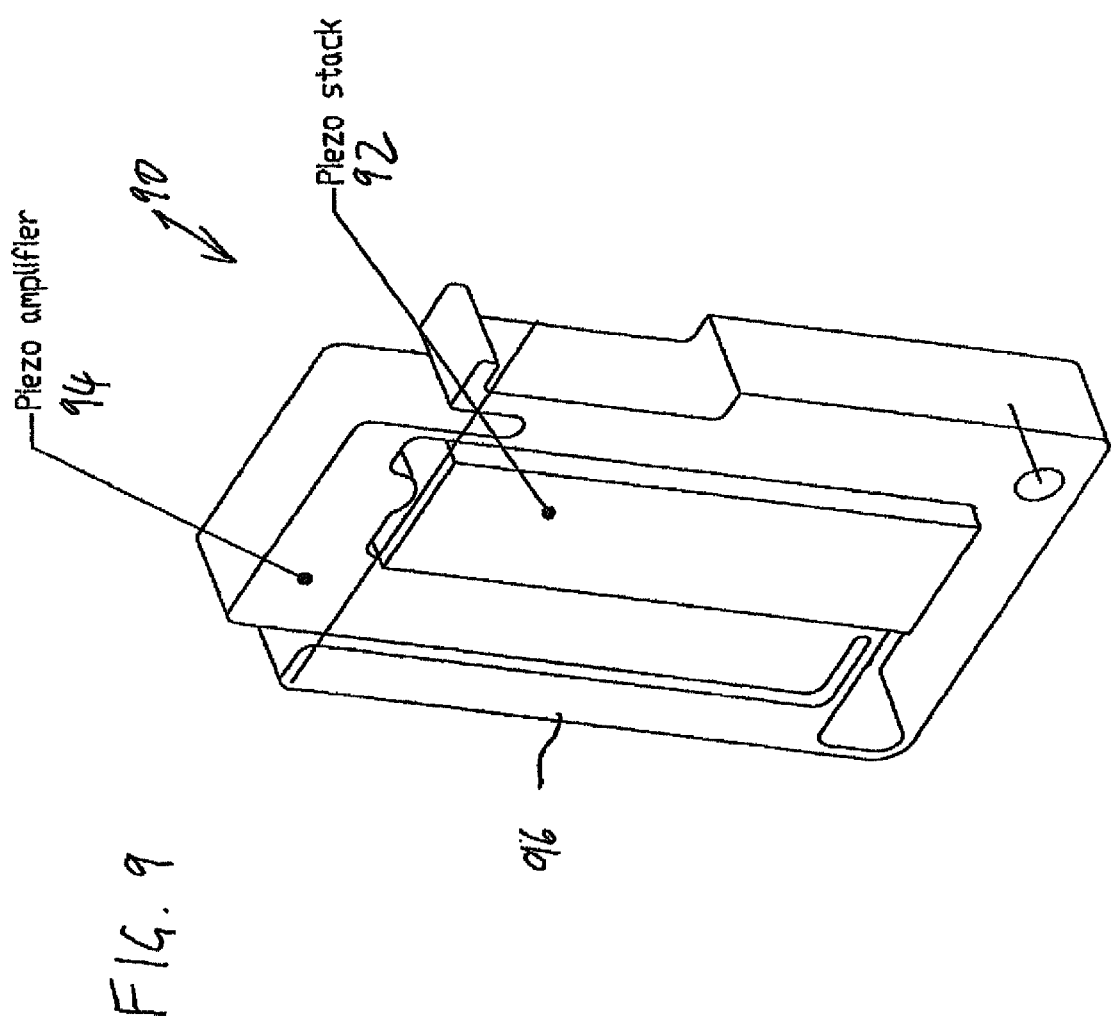
FIG. 9 is an enlarged isometric view of a piezoelectric actuator and mechanical amplifier shown in FIG. 7.

Actuator assembly 90 here includes a piezoelectric element 92, typically implemented as a stack of piezoelectric layers as is known in the art, electrically actuatable to generate a first displacement. Specifically, in the example shown here, the piezoelectric element is configured to elongate in the direction viewed here as "up-down". Deployed around piezoelectric element 92 is a mechanical amplifier 94 which is configured to convert the displacement of the piezoelectric element into a much larger output displacement of an output arm 96 for displacing actuator surface 74 of the valve. In this case, the output displacement is substantially perpendicular to the piezoelectric element's direction of elongation. It should be appreciated that a wide range of known mechanical amplifiers may be used in this device, although the implementation as shown in FIGS. 7 and 9, which is based upon three integral hinges and skewing of the associated triangular geometry, is believed to be particularly advantageous for its compactness and large amplification ratio. An alternative preferred implementation will be described with reference to FIGS. 19-23 below.

In addition to the enhanced range of displacement achieved by use of amplifier 94, it is typically preferable to provide an alignment adjustment for bringing the actuator assembly 90 into close engagement with the valve actuation surfaces prior to operation of the device. In a preferred implementation illustrated here, eccentric cams 100, detailed in FIG. 8, are mounted at two positions along a rotary shaft 102 turned by an adjustment knob 104. Each cam 100 is rotatably engaged with shaft 102 via an overriding clutch mechanism, typically based upon a spring-loaded ball 106, which defines a predefined maximum tightening torque transferable from the shaft to the cam. As a result, rotation of adjustment knob 104 simultaneously rotates both cams 100 so as to push the actuator assemblies 90 into close engagement with their corresponding actuator surfaces 74. Each actuator assembly is pushed forward until a predetermined mechanical resistance occurs at which point the overriding clutch prevents further transfer of torque to the cam. In this manner, a single rotating motion of adjustment knob 104 simultaneously achieves the appropriate extent of tightening motion independently for both actuator assemblies 90.

An alternative preferred implementation of actuator assemblies 200 is shown in FIGS. 19-23. Actuator assembly 200 is generally similar to the pair of actuator assemblies 90 described above, analogous elements being labeled similarly. This implementation differs from the implementation of FIGS. 7 and 9 primarily in that the adjustment mechanism is a self-adjusting arrangement which avoids the use of an overriding clutch mechanism. This implementation also exemplifies an alternative preferred mechanical amplifier structure where both mechanical amplifiers 94 are integrated into a unitary easily manufactured unit.

Specifically, as in actuator assemblies 90, assemblies 200 include piezoelectric elements 92 deployed to provide input for, and preferably set within, mechanical amplifiers 94 which generate an output displacement at output arms 96. This preferred implementation of mechanical amplifiers 94 is shown in more detail in FIG. 21. In this example, the mechanism is based on four integral hinges per amplifier. Both amplifiers 94 are preferably integrally formed, typically from a plate of spring steel by use of laser cutting or electro-erosion (wire cutting) techniques known in the art. This integral construction offers improved structural integrity and minimizes production costs.

Also shown in FIG. 21 are two clamping rods 202 which form part of the adjustment mechanism, as will be detailed below. Each clamping rod 202 has a clamping portion 204 and an abutment shoulder 206, here provided by a larger diameter portion of clamping rod 202.

Figure 19:
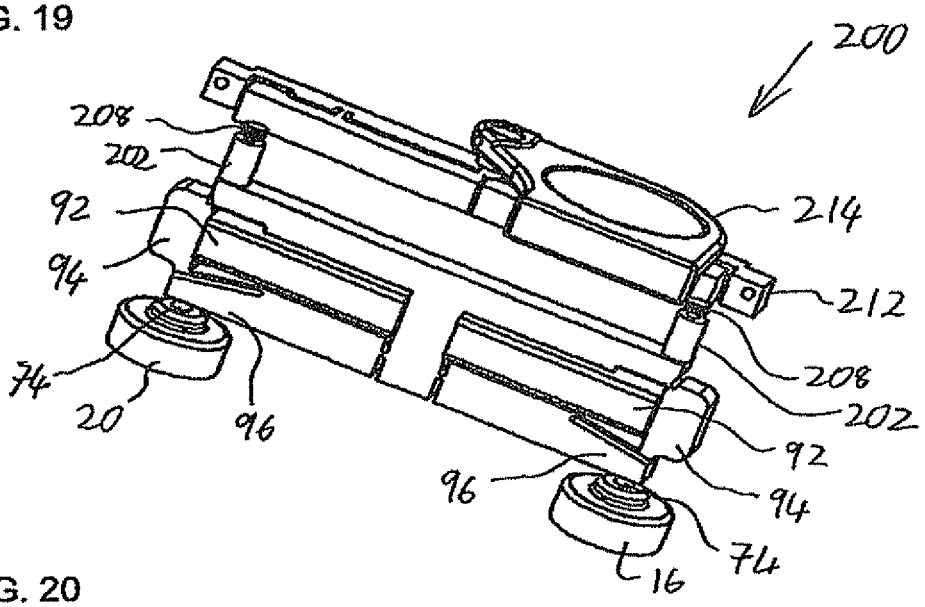
FIG. 19 is an isometric view of an alternative implementation of a piezoelectric actuator system for use in the drug delivery device of the present invention.
Figure 20:
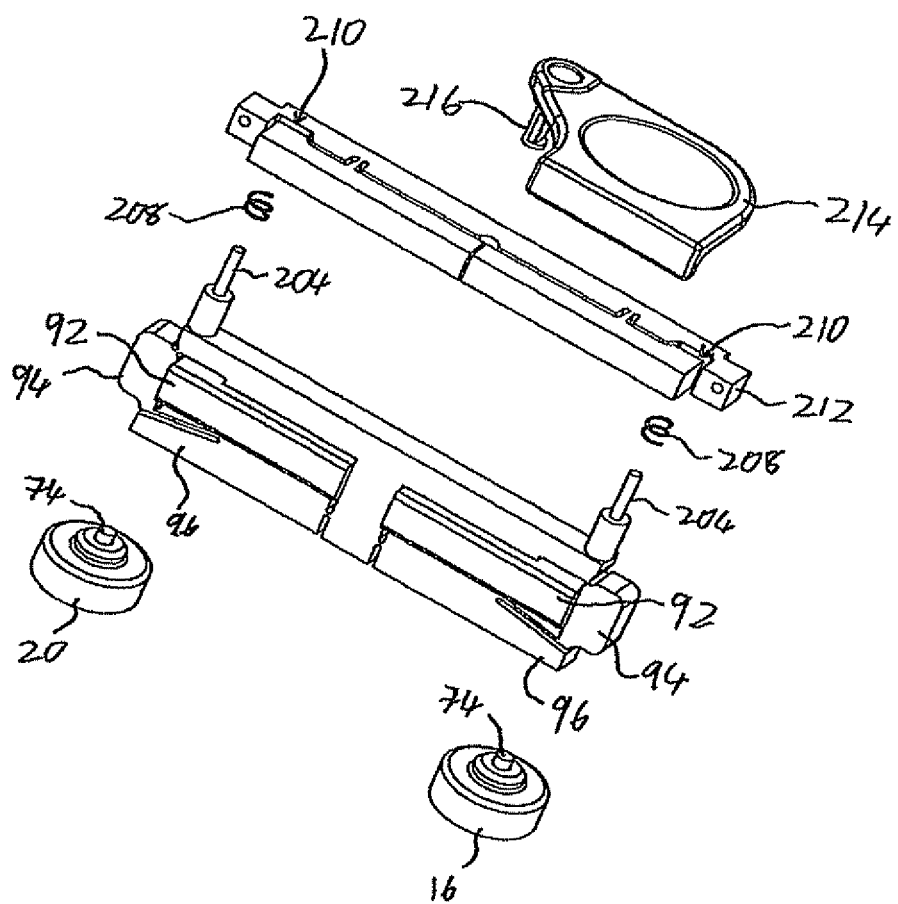
FIG. 20 is an exploded isometric view similar to FIG. 19.

The overall construction of the adjustment mechanism of actuator assembly 200 is best understood by reference to FIGS. 19 and 20. Each of clamping rods 202 receives a spring element 208 deployed on clamping portion 204 abutting shoulder 206, and clamping portions 204 are inserted into corresponding clamping gaps 210 of a clamping arrangement. The clamping arrangement itself is preferably made up of a double-lever clamping block 212 which is operated by a handle 214 which turns a cam-pin 216.

A preferred implementation of double-lever clamping block 212 is shown in FIGS. 22A and 22B. Clamping block 212 preferably has an elongated base 218 to which two lever arms 220 are pivotally connected at hinges 222. Here too, in a most preferred implementation, hinges 222 are integral hinges with elongated base 218, lever arms 220 and hinges 222 being integrally formed. Lever arms 220 are preferably also interconnected by an integral hinge. A recess 224 is positioned for receiving cam-pin 216 (shown enlarged in FIG. 23) such that rotation of handle 214 actuates clamping motion of both lever arms 220 simultaneously. Preferred materials for clamping block 212 include, but are not limited to, spring steel, typically processed by laser or electro-erosion technology. Other examples include various polymer materials, cut or molded to the required form.

In its assembled configuration, clamping portions 204 of rods 202 are inserted into clamping gaps 210 and elongated base 218 of clamping block 212 is attached to body 70. When handle 214 is in an open position such that cam-pin 216 does not actuate clamping of lever arms 220, clamping portions 204 are free to slide within clamping gaps 210. In this state, after insertion of a cartridge 72, compressed spring elements 208 bear on clamping block 212 and shoulders 206 so as to bias the mechanical amplifier assembly into contact with the two valve actuator surfaces 74. Spring elements 208 are chosen to be softer than the resilience of the valve assemblies themselves such that spring elements 208 absorb any free play between the actuator assembly and the valves, bringing each output arm 96 into contact with the corresponding valve actuator surface 74 without opening the valves. After insertion of the cartridge, handle 214 is then returned to a closed position, thereby turning cam-pin 216 and hence displacing both lever arms 220 simultaneously. The movement of the lever arms acts to close clamping gaps 210, thereby locking clamping portions 204 against movement and fixing the corresponding half of the actuator assembly relative to its valve ready for use.

Turning now to FIGS. 11 and 12, there is shown a preferred implementation of pressure measurement arrangement 22 which includes a differential pressure sensor 110 included within body 70. Differential pressure sensor 110 is in fluid connection with two connectors, implemented here as hollow needles 112. Removable cartridge 72 is formed with a pair of pressure sensing cells 114, best seen in the enlarged view of FIG. 12, each of which has a sensing volume 116 isolated from fluid in the flow path by a flexible membrane 118. Each sensing cell 114 has a complementary connector for mating with the pressure sensor connectors. In the case of hollow needles 112, the complementary connectors are preferably elastomeric seals 120 which can be pierced by needles 112. When removable cartridge 72 is engaged with body 70, each of the sensor connectors 112 mates with a corresponding complementary connector 120 such that the differential pressure sensor measures a differential pressure between liquid in the flow path at the first and second points without compromising sterility of the liquid medicament stored within the flow path defined by the disposable cartridge 72.

In order to ensure effective transfer of fluid pressure along the conduits between needles 112 and sensor 110, the pressure sensing cells 114, the conduits and needles 112 are preferably pre-filled with a liquid. The liquid is retained within needles 112 even when exposed due to capillary forces.

It will be appreciated that various other forms of self-sealing connectors may be used to interface between differential pressure sensor 110 and pressure sensing cells 114, as will be clear to one ordinarily skilled in the art. Nevertheless, the needle-based interface is believed to be particularly advantageous due to its small dead volume and its insensitivity to slight misalignments.

Turning now briefly to FIG. 13, this shows a preferred implementation of a filling port 126 for the pressurized storage reservoir 12. In the example shown here, port 126 is configured for filling by use of a standard needle and syringe. Although self-sealing ports for injection with a needle are well known per se, use of this filling technique for relatively high pressures is problematic due to the high occurrence of a quantity of drug spraying from the beveled end of the needle as it is withdrawn from the port. To address this problem, the preferred implementation of port 126 as shown here includes a primary elastomeric seal 130 and a secondary elastomeric layer 128 slightly spaced from the primary seal. The secondary layer 128 is preferably implemented as a disk which has a small range of free motion in the direction of insertion of a needle. During filling, a needle is advanced through both secondary layer 128 and primary seal 130 and the required volume of liquid medicament is injected into the reservoir.

Then, as the needle is withdrawn, it first clears the primary seal where any spray is released between the two sealing elements. As a result, when the needle is further withdrawn from the secondary layer 128, no further spraying of drug occurs. The ability of the disk to move axially within a cylindrical cavity is believed to cause slightly reduced pressure between the elements as the needle is withdrawn, thereby ensuring that any drug released between the elements is not at sufficient pressure to cause further spraying as the needle clears the secondary layer 128.

Figure 14C:
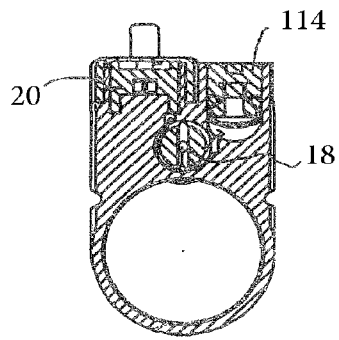
Figure 14D:
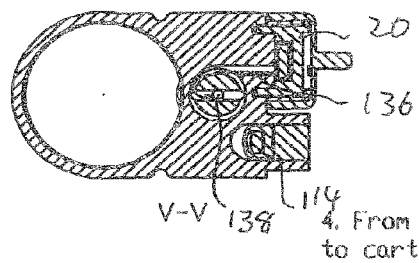
Figure 14A:
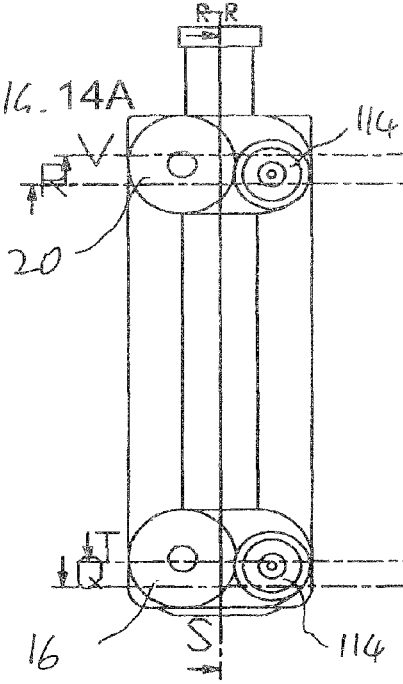
Figure 14B:
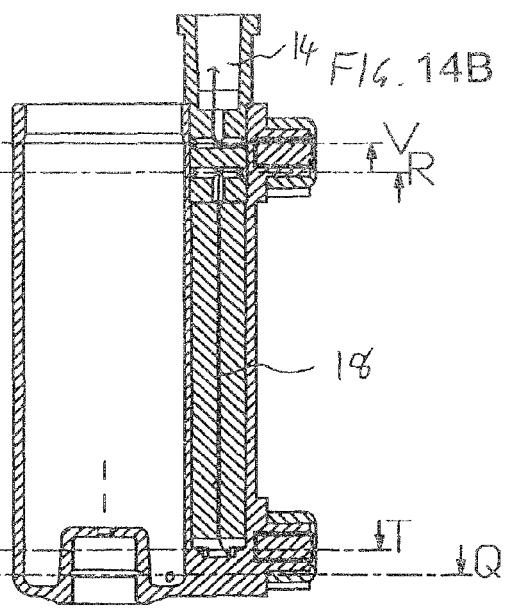
Figure 14E:
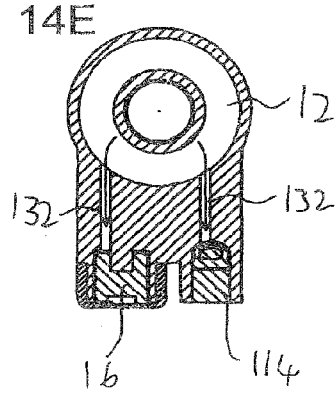
Figure 14F:
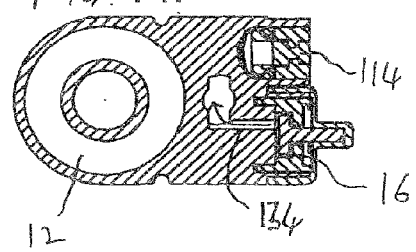

Turning now to FIGS. 14A-14F, these illustrate the overall flow path from the pressurized reservoir 12 to outlet 14 as defined by disposable cartridge 72. Firstly, as shown in FIG. 14E, two separate channels 132 extend from reservoir 12 to first valve 16 and lower pressure sensing cell 114. In this context, it should be noted that the pressure within the beginning of the flow path through the valves is essentially the same as that within the reservoir itself and, for this reason, measurement of the reservoir pressure is considered herein within the definition of pressure measurement at a "point within the flow path". The outlet 134 of valve 16 is seen in FIG. 14F as leading to the entrance to a capillary tube which provides flow restriction 18 (FIG. 14B). At the top of the capillary tube, the flow path splits towards upper pressure sensing cell 114 and second valve 20 (FIG. 14C). The output 136 of valve 20 returns to a vertical channel 138 (FIG. 14D) which connects to output 14.

Figure 4:
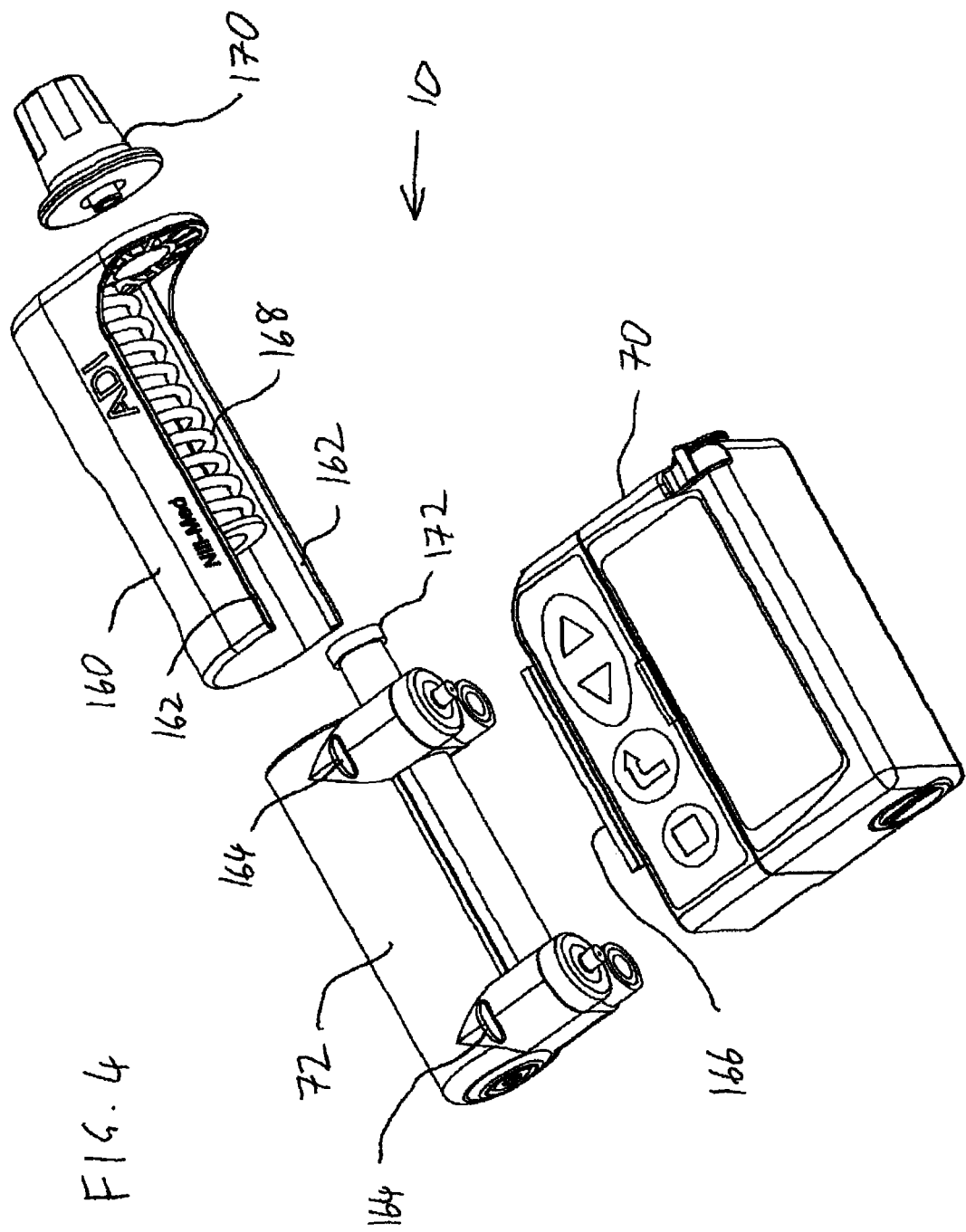
FIG. 4 is an isometric view of a preferred implementation of the drug delivery device of FIG. 1 including a body and a disposable cartridge.

Referring now briefly back to FIG. 4, this also shows a preferred configuration for interlocking disposable cartridge 72 with body 70. In the structure shown here, a sliding cover 160 is provided with a pair of inwardly projecting ridges 162 which engage corresponding slots 164 on cartridge 72 and a rail 166 on body 70. The spring 168 which provides pressurization of reservoir 12 is here shown mounted to cover 160 so that it is brought into position to bias a piston 169 when the slide is assembled as shown in FIG. 5. Once the body and cartridge are interlocked by sliding cover 160, a retaining nut 170 is attached to the outlet projection 172 of the cartridge, thereby locking the cover in place. Nut 170 is also configured to function as a connector for attachment of the fluid delivery infusion set (not shown).

Figure 15:
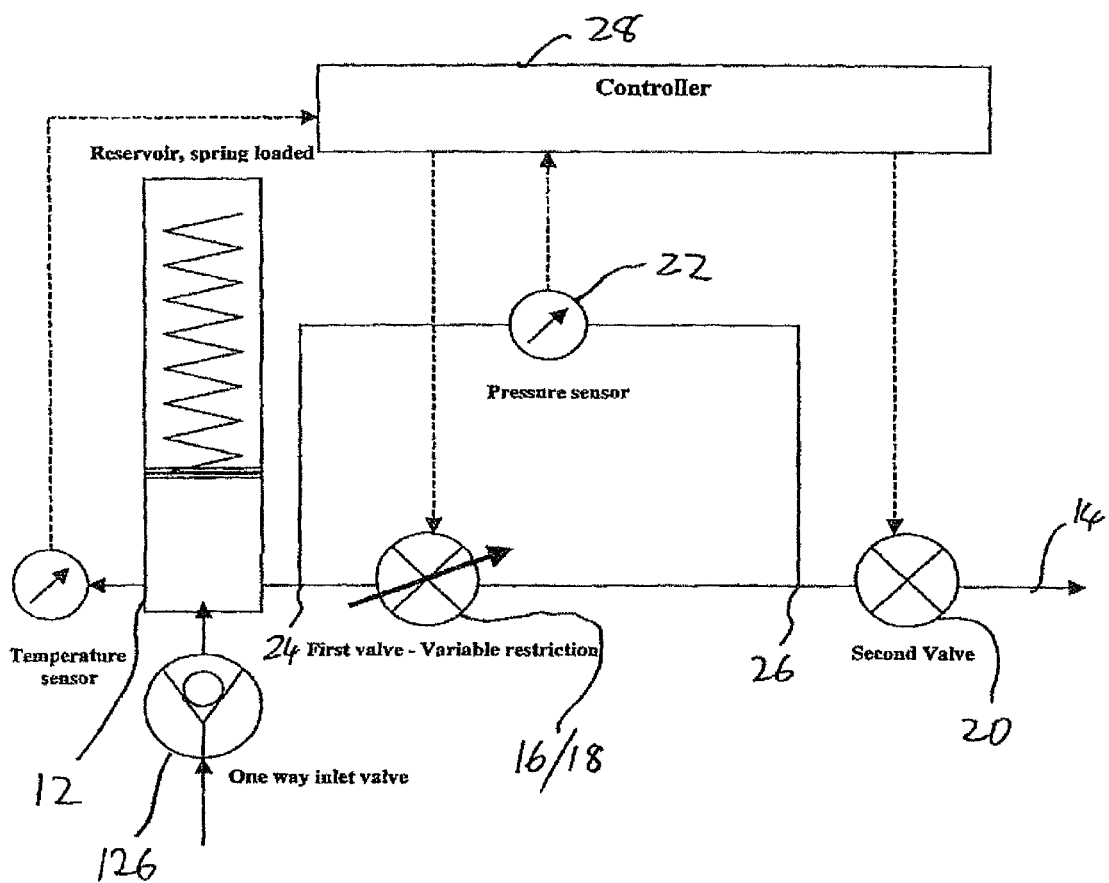
FIG. 15 is a schematic representation of a drug delivery device similar to FIG. 1 in which the first valve also provides a fluid flow restriction.

Turning now to FIG. 15, it should be appreciated that the function of flow restriction 18 can optionally be performed by precise control of a valve. In this case, it is possible to combine the functions of first valve 16 and flow restriction 18 into a single continuously controllable or multi-state valve 16/18. In all other respects, the structure and function of the device remain identical to that described above with reference to FIG. 1.

Figure 16:
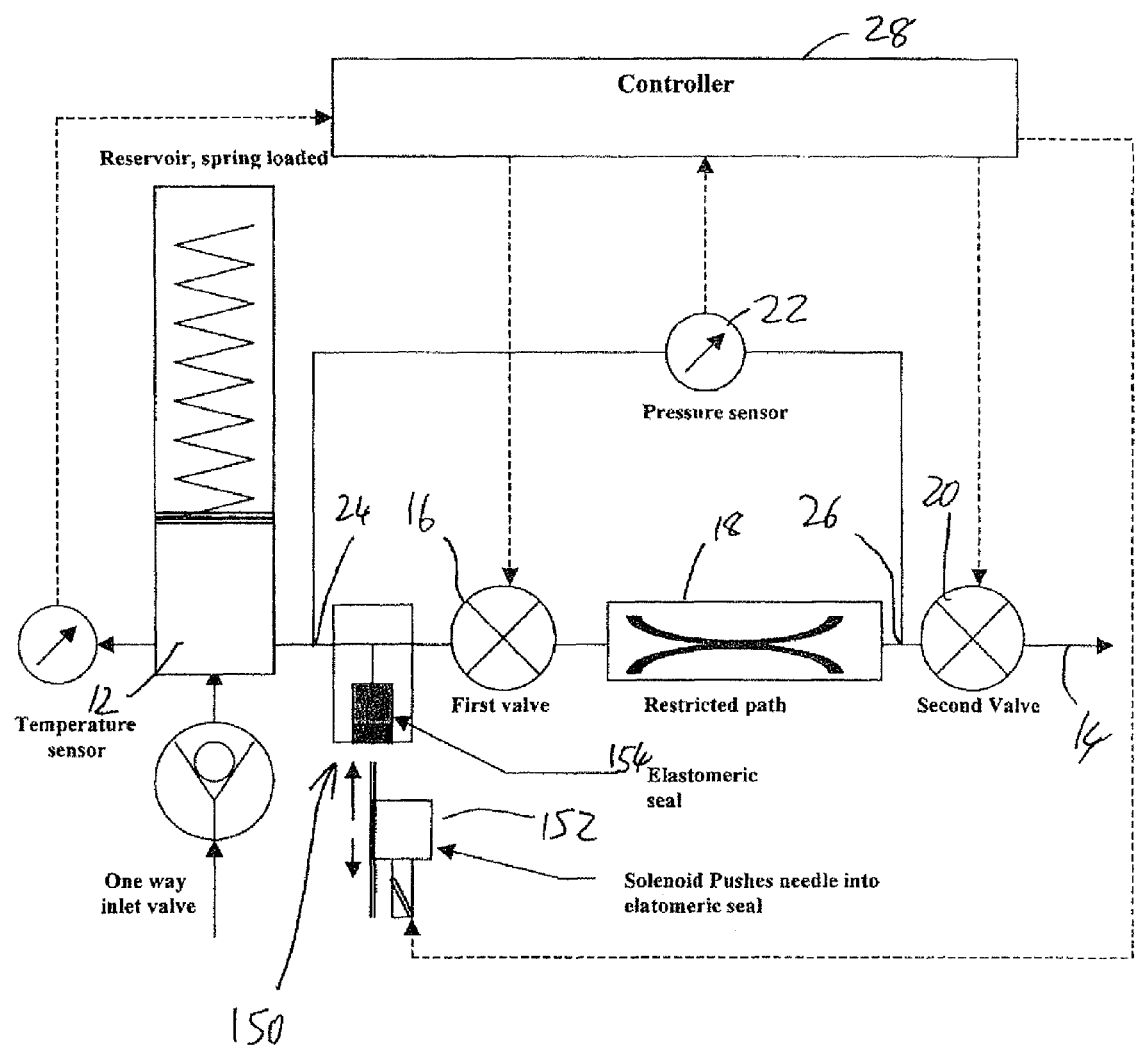
FIG. 16 is a schematic representation of a drug delivery device similar to FIG. 1 modified by addition of an emergency pressure release mechanism suited to external devices.
Figure 17:
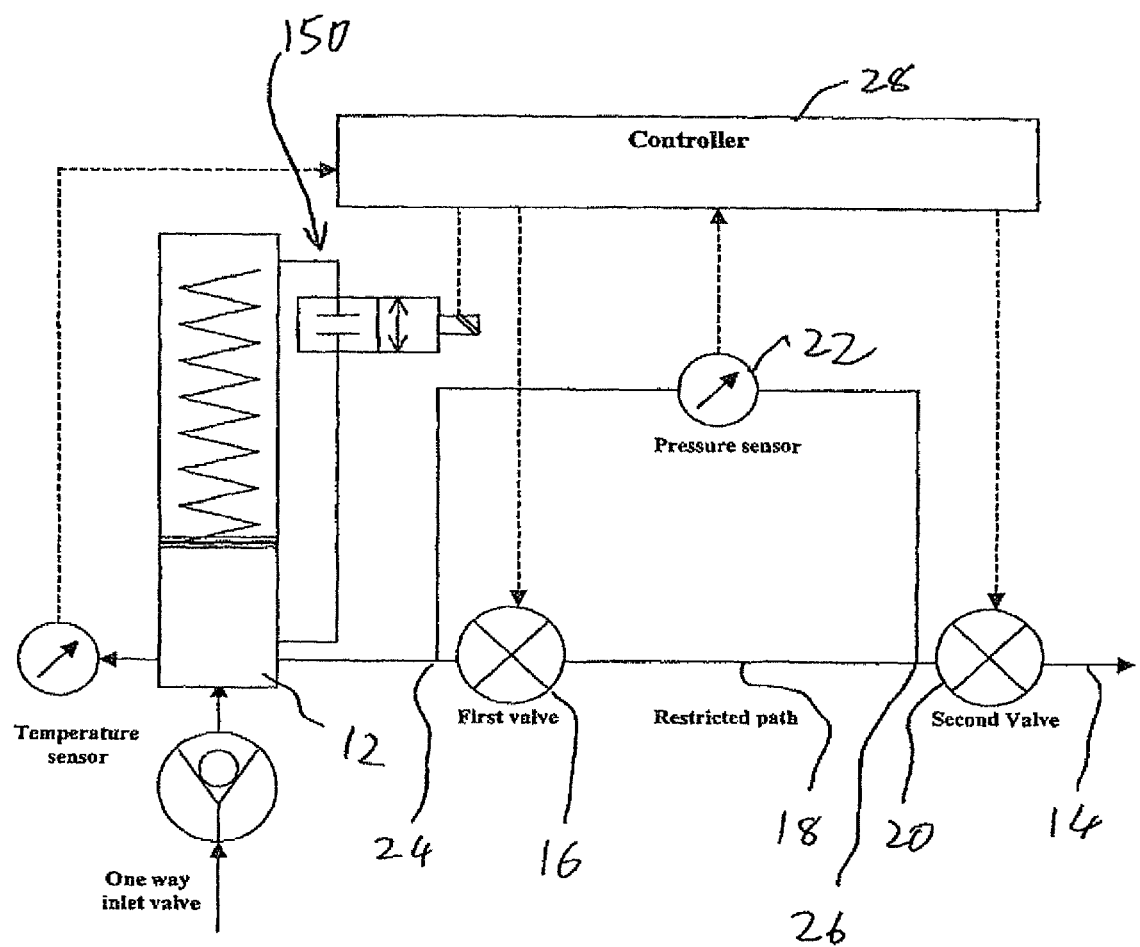
FIG. 17 is a schematic representation of a drug delivery device similar to FIG. 1 modified by addition of an emergency pressure release mechanism suited to both external and implantable devices.
Figure 18:
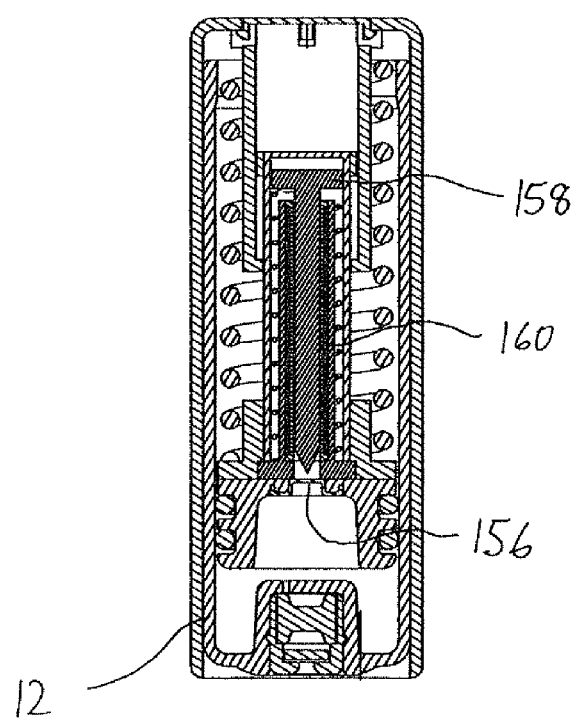
FIG. 18 is a cross-sectional view taken through a pressurized reservoir of the present invention illustrating a preferred implementation of the emergency pressure release mechanism of FIG. 17.

Turning now to FIGS. 16-18, these illustrate an additional optional feature which can be used to advantage with the device of FIG. 1. Specifically, although the double valve configuration and self-testing features of the present invention provide extremely effective safety precautions against overdosing, there remains at least a theoretical possibility that failure to properly address an alarm condition and/or multiple component failures could result in release of excess medication due to the pressure gradient from the reservoir to the subject's body. To address this issue, certain implementations of the present invention feature a reservoir pressure release mechanism 150 associated with controller 28 and selectively actuatable to depressurize reservoir 12 so as to deactivate delivery of the liquid medicament to outlet 14. Actuation of pressure release mechanism 150 is preferably triggered either by a persistent alarm condition which has continued for a predetermined time period without being remedied and/or immediately by predefined dangerous conditions such as the failure of the pressure sensor arrangement or the failure both valves to respond.

FIG. 16 represents schematically an implementation of pressure release mechanism 150 for an external drug delivery device. In this case, a solenoid actuated needle 152 is selectively advanced to puncture an elastomeric seal 154 located between the reservoir and the first valve. When actuated, the entire pressurized contents of reservoir 12 are released via the open-ended needle, thereby canceling the pressure gradient from the reservoir to the subject's body and preventing continued delivery of the drug.

FIG. 17 shows a similar system adopted so as to be suitable for both external and implantable devices. In this case, the region around the actuator spring of the reservoir is pre-sealed as a reduced-pressure cavity. In this case, pressure release mechanism 150 is implemented as a solenoid operated valve or frangible partition which, when actuated, allows fluid communication between the pressurized storage volume of the reservoir and the reduced pressure cavity in the spring volume. This allows the liquid medicament to bypass the spring-driven piston and fill the void behind the piston, thereby releasing the spring and canceling the pressure gradient from the reservoir to the subject's body.

Turning now to FIG. 18, this shows a preferred implementation of the pressure release mechanism of FIG. 17. In this case, the piston of the pressurized reservoir includes a diaphragm seal 156. Incorporated into the stem of the piston is a piercing pin 158 associate with a solenoid actuator 160. When the emergency pressure release mechanism is actuated via electrical connections (not shown) by controller 28, the solenoid actuator 160 draws piercing pin 158 downwards, thereby piercing the diaphragm and allowing escape of the pressurized liquid to a reduced pressure region in the volume of the cartridge above the piston.

It will be clear to one ordinarily skilled in the art that the pressure release mechanism such as is illustrated with reference to FIGS. 16-18 provides an additional back-up safety system applicable in other contexts which renders the use of pressurized reservoirs acceptable for a wide range of applications for which they would otherwise be ruled out for safety reasons.

It will be appreciated that the above descriptions are intended only to serve as examples, and that many other embodiments are possible within the scope of the present invention as defined in the appended claims.

What is claimed is:

1. A pressure measurement interface for measuring fluid pressure within a disposable arrangement defining a fluid flow path by use of a reusable pressure sensor, the interface including:
    (a) a disposable pressure sensing cell deployed in fluid connection with said fluid flow path, said pressure sensing cell including a closed liquid-filled sensing volume isolated from fluid in the fluid flow path by a flexible membrane, said sensing volume having a first portion of a mating configuration; and
    (b) a second portion of a mating configuration associated with the reusable pressure sensor and configured for mating with said first portion of said mating configuration so as to form fluid interconnection between the pressure sensor and said liquid-filled sensing volume, wherein the pressure sensor is a differential pressure sensor measuring a pressure differential between a first and a second measurement port, the interface further including a second disposable pressure sensing cell deployed in fluid connection with a second region in said fluid flow path and a second mating configuration for connecting between said second disposable pressure sensing cell and the differential pressure sensor.

2. The pressure measurement interface of claim 1, wherein said first portion of said mating configuration includes an elastomeric seal and wherein said second portion of said mating configuration includes a needle for piercing said elastomeric seal.

3. The pressure measurement interface of claim 2, wherein said needle is pre-filled with a liquid.

4. The pressure measurement interface of claim 1, wherein the disposable arrangement is a disposable cartridge for a fluid drug delivery device, and wherein the pressure sensor is mounted within a body configured for receiving said disposable cartridge.

* * * * *